United States Patent [19]

Hunnebeck

[11] Patent Number: 5,046,198
[45] Date of Patent: Sep. 10, 1991

[54] GAS GOGGLES

[75] Inventor: Volker Hunnebeck, Berlin, Fed. Rep. of Germany

[73] Assignee: Auergesellschaft GmbH, Berlin, Fed. Rep. of Germany

[21] Appl. No.: 526,581

[22] Filed: May 21, 1990

[30] Foreign Application Priority Data

Aug. 30, 1989 [DE] Fed. Rep. of Germany ....... 3928696

[51] Int. Cl.$^5$ ............................................. A61F 9/02
[52] U.S. Cl. ........................................ 2/440; 2/426; 2/441; 2/445; 351/178
[58] Field of Search ................... 2/426, 428, 429, 430, 2/440, 441, 442, 444, 445, 454; 351/43, 178

[56] References Cited

U.S. PATENT DOCUMENTS

| Re. 12,816 | 6/1908 | Cover | 2/428 |
| 1,388,959 | 8/1921 | Lamb et al. | 2/428 |
| 1,949,595 | 3/1934 | Willson et al. | 2/428 |
| 2,321,159 | 6/1943 | Ryan | 88/41 |
| 2,524,245 | 10/1950 | Wold | 2/428 |
| 2,799,020 | 7/1957 | Currie | 2/428 |
| 2,952,852 | 9/1960 | Corey | 2/429 |
| 3,800,329 | 4/1974 | Semeia | 2/428 |
| 4,606,670 | 8/1986 | Angell | 2/429 |
| 4,698,857 | 10/1987 | Kastendieck et al. | 2/426 |

FOREIGN PATENT DOCUMENTS

| 457339 | 6/1949 | Canada . | |
| 318647 | 6/1989 | European Pat. Off. | 2/426 |
| 675276 | 4/1939 | Fed. Rep. of Germany | 2/441 |
| 1158297 | 6/1958 | Fed. Rep. of Germany | 2/428 |
| 421744 | 3/1911 | France . | |

Primary Examiner—Werner H. Schroeder
Assistant Examiner—Michael A. Neas
Attorney, Agent, or Firm—Reed Smith Shaw & McClay

[57] ABSTRACT

The present invention describes goggles for protection against gases having a resilient frame with two eye spaces each surrounding an eye of the user. The eye spaces are surrounded by mounts which hold the lenses in place. In order to obtain a firm fit and the required sealing-tightness between the lenses and the mounts, the surface of the front edge of the mount is formed with a peripheral groove in which a rigid ring is secured. This ring applies pressure to the surface of the front edge of the mount sealingly securing the lens in a recess in the mount.

4 Claims, 1 Drawing Sheet

GAS GOGGLES

FIELD OF THE INVENTION

The present invention relates to goggles or safety eyeglasses for protection against gases which have a resilient frame with two eye spaces, each surrounded by mounts for holding a lens therein.

BACKGROUND OF THE INVENTION

In many goggles, the lenses are secured in the mounts in the frame around each eye space by clamps. The clamps are placed around the edge of the mounts and are secured thereto by the use of tightening or screw components which have to be suitably tightened by auxiliary tools to ensure a firm fit and obtain the required sealing-tightness between the lenses and the mounts. Tools are also necessary for changing the lenses if there is a defect or if the lenses become damaged. In addition, since the tightening and screw components are adjusted manually, there is a risk that the sealing-tightness between the lenses and the mounts will not be complete since this depends on careful fitting.

Other goggles and safety eyeglasses are shown and described in U.S. Pat. Nos. 4,698,857; 2,321,159; and 1,949,595; Reissue No. 12,816, as well as in Canadian Patent No. 457,339 and French Patent No. 421.744. These patents were cited in U.S. Pat. No. 4,908,394 filed Nov. 23, 1988 by the same applicant and inventor. In the goggles described in these references, the lenses are typically held in a recess in the mount only by the pliable and resilient nature of the mount. As a result, the lenses may be dislodged accidentally and over time may cease to have the required sealing-tightness as the mounts become less pliable.

It would be desirable to construct a pair of goggles wherein the lenses are firmly and sealing-tightly held in the mounts by a simple and effective means, thereby obviating the disadvantages of the above-described goggles.

SUMMARY OF THE INVENTION

Generally, the present invention pertains to safety eyeglasses. The safety eyeglasses protect a user against gases. The eyeglasses include a pliable frame having a separate eye space surrounding each eye of a user. A lens for each eye space is held in place by a mount. Each mount externally surrounds the outer edge of the corresponding lens and eye space, and has a front edge, a rear edge and a recess therebetween, the latter for receiving the outer edge of the lens. A peripheral groove is formed on the surface of the front edge of each mount and a rigid ring is nondetachably secured in the groove thereby sealingly holding the lens in the recess of the mount. An advantage of the present invention is that the lenses are firmly sealed and tightly clamped in the mounts without using manually adjusted tightening or screw components.

Preferably, the frame also has a single fold bellows for each eye space as more particularly described and shown in U.S. patent application Ser. No. 07/267,217 filed Nov. 23, 1988, the disclosure of which is incorporated herein by reference as if fully set forth herein.

Other details, objects and advantages of the present invention will become apparent as the following description of the presently preferred embodiment of practicing the invention proceeds.

BRIEF DESCRIPTION OF THE DRAWING

In the accompanying drawing, a preferred embodiment of the present invention is illustrated, by way of example only, wherein.

DESCRIPTION OF THE PREFERRED EMBODIMENT

Figure 1:
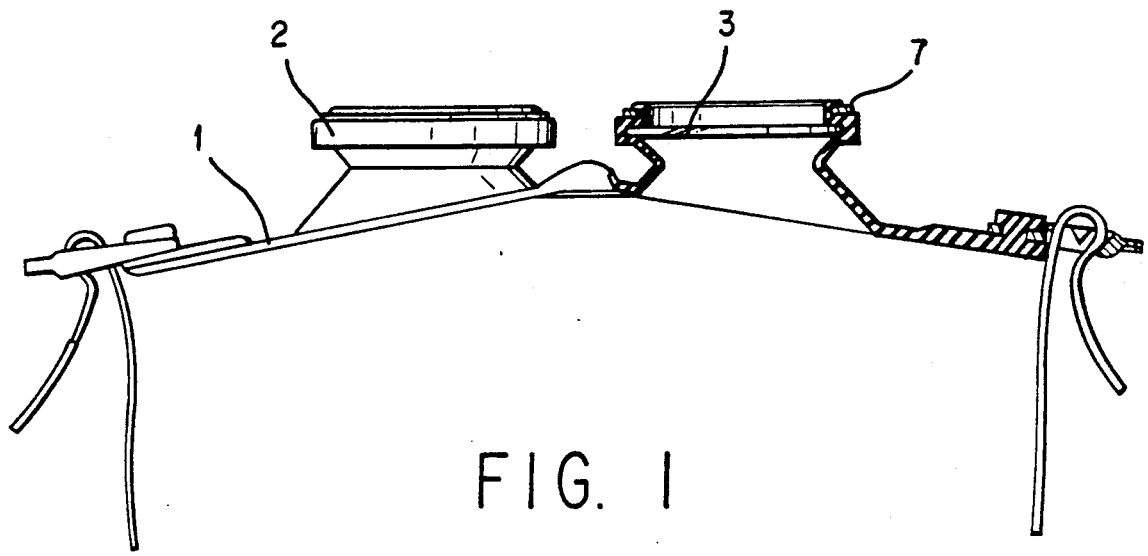
FIG. 1 is a plan view of the goggles of the present invention partly in elevation and partly in section.
Figure 2:
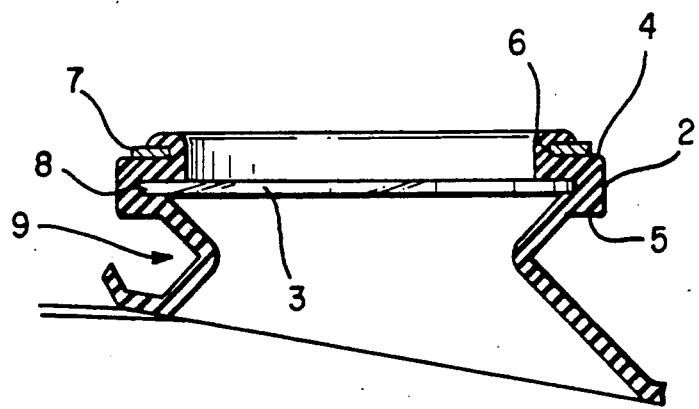
FIG. 2 is a close-up of the sectional portion of FIG. 1 showing the mount and lens.

As shown in FIGS. 1 and 2, safety eyeglasses substantially comprise a frame 1, made of a resilient and/or pliable material, with a mount 2 for holding each lenses 3 and a bellows 9 for permitting the eyeglasses to be stored in a compact manner. Advantageously, each mount 2 externally surrounds the outer edge of the corresponding lens 3, and has a front edge 4, a rear edge 5 and a recess 8 therebetween, the latter for holding the outer edge of lens 3. A peripheral groove 6 is formed on the surface of the front edge 4 and a ring 7 is fastened therein. Preferably, ring 7 is a flat disc which is inserted into the groove 6 such that it uniformly presses the front edge 4 of mount 2 with prestressing against the lens 3 that has been inserted into recess 8. As a result, the lens 3 is nondetachably secured in the mount 2 and also tightly sealed therein.

While a presently preferred embodiment of practicing the invention has been shown and described with particularity in connection with the accompanying drawings, the invention may otherwise be embodied within the scope of the following claims.

What is claimed is:

1. Safety eyeglasses which protect against gases comprising: a resilient frame with two eye spaces, each one for surrounding an eye of a user; a lens for each eye space which is held therein by a mount; wherein each mount externally surrounds an outer edge of the corresponding lens and has a front edge, a rear edge and a recess therebetween for receiving the outer edge of the lens; wherein a peripheral groove is formed on the surface of the front edge of each mount; and wherein a flat rigid ring of substantially rectangular cross-section and having an inside diameter smaller than an outside diameter of the lens is removably secured in the peripheral groove thereby sealingly holding the lens in the recess.

2. The safety eyeglasses as described in claim 1 wherein the rigid ring is a flat disc removably inserted into the groove such that it presses the front edge of the mount against the lens inserted into the recess to secure and seal it therein.

3. The safety eyeglasses as described in claim 2 wherein the flat disc uniformly presses the front edge of the mount against an outer surface of the lens.

4. The safety eyeglasses as described in claim 1 wherein the resilient frame comprises a bellows surrounding each eye space.

* * * * *